United States Patent [19]

Brooks, Jr. et al.

[11] Patent Number: 5,514,602

[45] Date of Patent: May 7, 1996

[54] METHOD OF PRODUCING A METAL SOL REAGENT CONTAINING COLLOIDAL METAL PARTICLES

[75] Inventors: Houston G. Brooks, Jr., Somerset; Chi-Deu Chang, Bridgewater; Utpal R. Chakraborty, Flemington; Henry A. Graham, Jr., Annandale; Lloyd L. Hollenbeck, Jr., Flemington; Sharon R. Lawler, Somerville; Jennifer Nasser, Piscataway; Ernest G. Schutt, Long Valley, all of N.J.; Albert Venturini, E. Stroudsburg, Pa.

[73] Assignee: Ortho Diagnostic Systems, Inc., Raritan, N.J.

[21] Appl. No.: 22,544

[22] Filed: Feb. 25, 1993

Related U.S. Application Data

[63] Continuation of Ser. No. 437,977, Nov. 16, 1989, abandoned, which is a continuation-in-part of Ser. No. 273,640, Nov. 17, 1988, abandoned, which is a continuation of Ser. No. 872,357, Jun. 9, 1986, abandoned.

[51] Int. Cl.$^6$ .................................................. G01N 33/553
[52] U.S. Cl. .................. 436/525; 427/216; 427/388.1; 427/388.2; 427/388.3; 427/414; 436/518; 436/524
[58] Field of Search ..................................... 436/518, 524, 436/525, 529, 532, 808; 435/975; 427/216, 388.1, 388.2, 388.3, 414

[56] References Cited

U.S. PATENT DOCUMENTS

| | | | |
|---|---|---|---|
| 4,179,404 | 12/1979 | Barone | 502/209 |
| 4,313,734 | 2/1982 | Leuvering | 23/230 |
| 4,654,322 | 3/1987 | Holbein et al. | 502/401 |
| 4,677,057 | 6/1987 | Curtiss et al. | 435/7.92 |
| 4,775,636 | 10/1988 | Moeremans et al. | 436/518 |
| 4,920,061 | 4/1990 | Poynton et al. | 436/518 |

FOREIGN PATENT DOCUMENTS 0140489  5/1985  European Pat. Off. .

OTHER PUBLICATIONS

Weiser, H. B. "The Colloidal Elements", Inorganic Colloid Chemistry, J. Wiley & Sons (1933), pp. 1–107.

Geoghegon, W. D. "Immunoassays at the Microscopic Level: Solid Phase Colloidal Gold Methods", J. Clin Immunoassay 11(1):11–23.

Horisberger, M. "Colloidal Gold: A Cytochemical Marker for Light and Flourescent Microscopy and for Transmission and Scanning Electron Microscopy" SEM, 11:9–31 (1981).

Goodman, S. L. et al. "A Review of the Colloidal Gold Marker System" SEM 11:133–146 (1980).

Frens, G. "Controlled Nucleation for the Regulation of the Particle Size in Monodisperse Gold Suspensions" Nature Physical Sci. 241:20–22 (1973).

Roth, J. "The Colloidal Gold Marker System for Light and Electron Microscopic Cytochemistry".

Janssen Manual "Colloidal Gold Sols for Macromolecular Labelling" (1985).

Allinger et al., Organic Chemistry, Worth Publishers, Inc. (1971).

Orchin et al., The Vocabulary of Organic Chemistry, John Wiley & Sons, New York (1980).

Morrison and Boyd, Organic Chemistry, Fourth Edition, New York University, Allyn and Bacon, Inc. (1983).

Particle Technology Division of Seradyn Inc., "Microparticle Immunoassay Techniques", 1988 pp. 29–31.

Clark, John M. and Switzer, Robert L., "Experimental Biochemistry" 2nd Ed. 1977, (New York: W. H. Freeman and Company), pp. 72–73.

*Primary Examiner*—James C. Housel
*Assistant Examiner*—Christopher L. Chi
*Attorney, Agent, or Firm*—Woodcock Washburn Kurtz Mackiewicz & Norris

[57] ABSTRACT

A method and test kit useful in a wide variety of immunoassay systems. A method of producing metal sol reagents containing metal sol particles of a preselected size is provided. A metal containing solution is reduced under optimized pH conditions to produce metal sol particles of a preselected size, the particles are coated with a coupling compound and then bound with at least one selected immunochemically reactive component. Particles having different immunochemical specificities are also mixed to produce reagents having multiple selected immunochemical specificities.

5 Claims, No Drawings

METHOD OF PRODUCING A METAL SOL REAGENT CONTAINING COLLOIDAL METAL PARTICLES

This application is a continuation of U.S. Ser. No. 07/437,977, filed Nov. 16, 1989, abandoned, which in turn is a continuation-in-part of U.S. Ser. No. 07/273,640, filed Nov. 17, 1988, abandoned, which in turn is a continuation of U.S. Ser. No. 06/872,357, filed Jun. 9, 1986, abandoned, each of which applications are assigned to the assignee of the present invention and each of which are hereby incorporated by reference into the present application.

FIELD OF THE INVENTION

The invention related to a method for the production of metal sol reagents having particles of a preselected size useful in a variety of immunoassay systems and for use in microscopic techniques.

BACKGROUND OF THE INVENTION

Colloidal solutions or sols can be formed by condensation processes. Conventionally, a reducing agent is added to a metal salt forming metallic particles.

The most frequently employed method for preparing gold hydrosols is the reduction of chloroauric acid with a suitable reducing agent. A number of reducing agents can be used including formaldehyde, hydrogen peroxide, phosphorus, substituted ammonias such as hydroxylamine and hydrazine. Methods of production of gold sols are generally discussed in Roth, J. "The Colloidal Gold Marker System for Light and Electron Microscopic Cytochemistry" In Bullock, G. R. and Petrusz, P. (eds.), *Techniques in Immunocytochemistry* 2, pp. 217–284; Horisberger, M. "Colloidal Gold: A Cytochemical Marker For Light and Fluorescent Microscopy and For Transmission and Scanning Electron Microscopy", SEM 11:9–31 (1981); Weiser, H. B., "The Colloidal Elements", in *Inorganic Colloid Chemistry*, J. Wiley & Sons (1933), pp. 1–107.

Gold particles ranging in size from 2–140 nm are readily produced by a variety of methods. See Geoghegon, W. D. "Immunoassays at the Microscopic Level: Solid-Phase Colloidal Gold Methods", J. Clin Immunoassay 11(1):11–23 (1988). Using trisodium citrate as a reductant, particle diameter has been found to be a function of the quantity of citrate added. See Frens, G. "Controlled Nucleation for the Regulation of the Particle Size in Monodisperse Gold Suspensions", Nature Physical Sci. 241:20–22 (1973). Particle size may be varied over an approximate size range of 15–140 nm by varying the amount of citrate added. Particles in the 2–20 nm range can be produced using white phosphorus, ascorbic acid, or a mixture of tannic acid and citrate as the reductant.

Colloidal gold can be used as a particulate marker for the detection and localization of target molecules by various modes of microscopy using both direct and indirect labelling approaches. Under appropriate conditions, colloidal gold will bind macromolecules by non-covalent electrostatic adsorption with little change in the specific activity of the bound macromolecule. Interaction is influenced by ionic concentration, pH conditions in correlation with protein isoelectric points and protein stabilizing levels.

Under appropriate conditions, metal sol particles can be labelled with a variety of macromolecules, including polysaccharides, glycoproteins, proteins, lectins and antibodies.

Whenever the term "metal sol particles" is used in this application, this is understood to mean particles of a sol consisting of a metal or transition metal, a metal or transition metal compound or polymer nuclei coated with a metal or transition metal or a metal or transition metal compound. The metal sols may be of metals or transition metals or compounds thereof such as oxides, hydroxides, and salts or, of polymer nuclei coated with metals or transition metals or compounds thereof. Examples include platinum, gold, silver, iron, copper, selenium, chromium, vanadium, titanium, manganese. In addition, it is recognized that a metal sol produced in accordance with the teachings of Applicants' invention may be converted to a suspension of insoluble metal salts, sulphides, oxides, hydroxides or similar compounds. In general, all metals, transition metals or compounds thereof, which may be readily demonstrated by means of techniques well known in the art are within the scope of Applicants' invention.

For a general discussion concerning gold particle labelling techniques, see Horisberger, M. "Colloidal Gold: A Cytochemical Marker For Light and Fluorescent Microscopy and For Transmission and Scanning Electron Microscopy" SEM, 11:9–31 (1981). In most cases there is little change in the bioactivity of the adsorbed molecules. Generally, these probes acquire the specific activity of the adsorbed macromolecule and their stability upon storage is good. However, when gold particles are labelled with proteins, full stabilization against coagulation by electrolytes is not always observed, especially with larger size markers. A number of stabilizing agents including polyvinylpyrrolidone, poly-L-lysine, poly-L-proline, polyethylene glycols (PEG), and Carbowax have been suggested.

As probes, gold particles are particularly interesting because their electron dense properties allow detection by transmission electron microscopy (TEM), their capability of strong emission of secondary electrons allows visualization by scanning electron microscopy (SEM), their characteristic X-ray signals allow identification of gold markers on cell surfaces. In addition, gold probes are also useful in fluorescent microscopy by labelling gold particles with fluorescent molecules. Gold particles bound to a cell surface appear as an orange-red coating and are therefore useful in photonic microscopy and in macroscopic observations. The advantages of gold probes are discussed generally in Horisberger, M. "Colloidal Gold: A Cytochemical Marker For Light and Fluorescent Microscopy and For Transmission and Scanning Electron Microscopy", SEM, 11:9–31 (1981); Goodman, S. L. et al. "A Review of the Colloidal Gold Marker System", SEM 11:133–146 (1980) A bibliography of gold probe labelling studies is provided by Goodman, at page 139.

It has been shown that it is possible to select and adsorb a specific substance to colloidal gold to optimize its use as a tracer for electron microscopy (EM). It has been suggested that an ideal tracer substance should be available in a wide range of uniform sizes with an electron scattering core surrounded by a coat that could be varied as needed. See Geoghegon, W. D. "Immunoassays at the Microscopic Level: Solid-Phase Colloidal Gold Methods", J Clin Immunoassay 11(1):11–23 (1988). The gold is stabilized by a variety of substances, including polypeptides, polynucleotides, polysaccharides and organic polymers.

There are a number of immunoassays employing colloidal gold. The presence of a reactive protein on a probe can be demonstrated and quantitated by direct and indirect radioactive binding assays and agglutination assays. See Goodman, S. L. et al. "A Review of the Colloidal Gold Marker System", SEM 11:133–146 (1980).

To make a gold probe, the following basic steps are followed: a protein solution and colloidal gold are pH adjusted to optimize protein adsorption, the minimal protecting amount of protein is determined, the appropriate amount of protein is mixed with the colloidal gold and a secondary stabilizer added. The gold probe can then be purified and its concentration adjusted to a predetermined optical density. Using these general principles, ligands can be bound to gold probes for use in immunoassays. The Janssen manual entitled "Colloidal Gold Sols for Macromolecular Labelling" (1985) discloses basic probe construction techniques.

U.S. Pat. No. 4,313,734 (Leuvering) discloses a metal sol particle immunoassay. Leuvering teaches the preparation of a gold sol by reducing chloroauric acid with trisodium citrate to produce gold particles with diameters of 45–70 nm. The particles are then labelled with a rabbit anti-HPL serum by adjusting the sol to pH 7.0 with potassium carbonate and then adding a rabbit anti-HPL immunoglobulin solution. The coated gold particles can then be used for determination of HPL by colorimetry or atomic adsorption spectrophotometry. Leuvering also discloses the visual detection of hepatitis B surface antigen (HBsAg) by means of a gold particle sheep anti-HBsAg immunoglobulin conjugate. In this method the gold sol and the gold-immunoglobulin conjugate are prepared as before with the exception that a diluted solution of the sheep anti-HBsAg immunoglobulin solution was used instead of the rabbit anti-HPL immunoglobulin solution. Leuvering also discloses the determination of HCG with the aid of a gold particle-anti-HCG conjugate in an agglutination test. The gold sol and gold particle anti-HCG conjugate are prepared using the previously described methods. A competitive receptor assay for HCG is also disclosed. A gold dispersion consisting of particles having a diameter between 6–15 nm is prepared by adding sodium citrate to a boiling solution of chloroauric acid. A dialyzed HCG solution was added to the gold dispersion. The mixture was stabilized with Carbowax. A sandwich assay for HCG using an insolubilized HCG receptor and the gold particle-anti HCG conjugate is then performed.

U.S. Pat. No. 4,775,636 (Moeremans et al.) discloses a blot overlay assay using colloidal metal particles, preferably 3–100 nm in size. Moeremans et al. teach the use of a dispersion of a metal or metal compound or nuclei coated with a metal or metal compound as one detection principle in blot overlay techniques. Colloidal metal particles, including gold particles are prepared following art-known procedures. The colloidal metal particles can then be attached directly or indirectly to the specific binding agent or to a macromolecule that binds specifically to the first specific binding agent using known art procedures. Moeremans et al. find that colloidal metal particles so prepared will accumulate at the specific binding sites and surprisingly become visible as the color characteristic for the colloidal metal particles used, e.g. from pink to a dark red color, in the case of gold. The signal is read by eye or using spectrophotometric procedures.

SUMMARY OF THE INVENTION

The present invention relates to a chemical coupling process whereby colloidal metal particles, in particular colloidal gold sols, can be attached to specific binding proteins or immunochemically reactive components. These immunochemically reactive components include; immunoglobulins both polyclonal and monoclonal antibodies, immunochemically-active fragments of immunoglobulin antibodies, anti-antibodies, acceptor proteins such as antigens, haptens, and haptens that have been coupled to immunochemically inert carrier macromolecules, lectins, polysaccharides, enzymes, serum proteins, hormones, glycoproteins, peptides including recombinant proteins and polypeptides, DNA and RNA nucleotide sequences, including recombinant oligonucleotide sequences.

This unique coupling process allows the immunochemically reactive component to be attached to the surface of the colloidal gold particles with retention of much of the original reactivity.

An important aspect of the current invention is the coating of colloidal gold particles with glutaraldehyde under low pH conditions. This sets the stage for attachment of the immunochemically reactive component. The concentration of the glutaraldehyde with respect to the colloidal gold surface areas is an important aspect of this process.

A substantial size range of colloidal gold may be utilized including from about 20 nm to about 92 nm with a preferred size within the range of 30 to 60 nm and the most preferred size approximately 35 to 50 nm. A substantial variety of colloidal gold sizes as measured by the optical density ratio of 540 nm over 600 nm may be utilized including from about 1.7 (large particles) to 3.5 (small particles) with a preferred ratio within the range of 2 to 2.5. Colloidal gold particles in the preferred size range may be visually observed as a reddish blue color when in solution.

While the best mode contemplates direct labelling of the immunochemically reactive component with colloidal gold, it is also contemplated that equivalent indirect labelling may be employed and even preferred in certain circumstances. Such indirect labelling would typically utilize a third immunoglobulin which is itself labelled with the colloidal gold and is specifically reactive with the second immunoglobulin, in turn specific for the ligand to be detected. Such methods are particularly useful for antibody tests using anti-globulin labelled colloidal gold. Again, indirect labelling procedures are subjects readily understood by those skilled practitioners in the art.

These colloidal gold particles thus labelled with the specific immunochemically reactive component are used as specific reagents in multiple immunoassay detection systems.

An important advantage is provided by the present invention in that this chemical coupling process enhances the stability of these colloidal gold reagents and it allows them to function effectively in concert with a wide variety of stringent immunoassay conditions.

The method in accordance with the present invention is particularly suitable for the qualitative and/or quantitative determination of an immunochemically reactive component, such as a hapten, antigen, or antibody present in an aqueous test medium.

For this reason the invention similarly relates to the new immunological reagents consisting of an aqueous dispersion of metal sol particles to which either directly or indirectly an immunochemically reactive component has been attached.

The invention similarly relates to new test kits containing such an immunological reagent.

These and other objects of the present invention will become apparent from the following, more detailed description and is illustrated in its specific embodiment in the accompanying drawings.

DETAILED DESCRIPTION OF THE INVENTION

The present invention provides a novel chemical coupling process whereby colloidal metal particles, in particular colloidal gold sol, are attached to specific binding proteins or immunochemically reactive components. This novel process enhances the functionality of the colloidal gold reagents through the strong bonding of the immunochemically reactive component to the colloidal gold sol. Consequently, these reagents may be used in many diverse buffers having high ionic strength and a broad acceptable pH range i.e., pH 4.4 to 10.0. In addition, these reagents will function in a buffer system containing high salt molarities. Buffer additives such as detergents (e.g., Triton 705, Tween 20) or chaotrophic agents may also be used with these reagents without altering their immunochemical functionality. These reagents thus maintain increased stability in rather stringent immunoassay buffer environments.

The reagents prepared by the process of the present invention may be lyophilized to increase their stability. Likewise, they may also be air dried or lyophilized on the surface of an immunoassay's solid phase component, e.g., cellulose strips, paper, membranes, nitrocellulose sheets and devices. The reagents retain their biological activity and immune specificity as well as good colloidal character after rehydration and resuspension into an aqueous buffered medium.

A reagent of the present invention is prepared in accordance with the following general method.

In a three-necked round-bottomed flask (or an appropriate glass reactor, depending on the scale of preparation) fitted with an overhead stirrer, a nitrogen inlet tube and a temperature sensor, the colloidal gold particles (raw sol) are prepared from hydrogen tetrachloroaurate trihydrate (0.1 g, Aldrich Chemical Co.) and malic acid (0.2 g, Aldrich) at a pH range of 4.0–5.5 at 70°–95° C. for 1 hour. In this manner, one liter of raw, uncoated gold sol is prepared whose mean particle size is between 30 and 60 nm. The ratio of spectrophotometric absorbance at 540 nm to that at 600 nm is approximately around 1.8–3.5 under these conditions.

After cooling the sol to room temperature, the pH is adjusted to 5.0–9.0 with a 0.1 N KOH solution. 10 uL of an aqueous 25% glutaraldehyde solution (Polysciences, Inc., EM Grade) is then added, and stirred at room temperature for 45–120 minutes. The antibody or antigen to be coupled, or coated is taken up in a buffer containing 0.1M sodium phosphate and 0.1% sodium azide, pH 5–9. These components are then added to the gold sol and stirred for 0.5–5.0 hours minutes at room temperature. The Schiff's base thus generated is next reduced by adding solid sodium borohydride (50–90 mg) to the sol while stirring is continued for 5–30 minutes. The addition of borohydride is followed immediately by the addition of 40 ml sodium phosphate (0.1M)—sodium azide (0.1%) buffer, pH 6.0.

After the reduction was complete, a 1% Carnation nonfat dry milk solution in 0.1M sodium phosphate-0.1% sodium azide, pH 7.0 buffer is added (10 ml), and stirred overnight. Bovine serum albumin (BSA) of various grades (RIA, Fr. V, monomeric, etc.) may also be used as a blocking agent. The coated gold sol (dye reagent) is then centrifuged at 5°–10° C. at about 8,000–10,000 rpm for 20 minutes. The supernatant liquid is then removed, and the residual dye particles are re-suspended in an appropriate buffer. This process is repeated twice in order to wash the dye thoroughly with the working or final buffer. The amount of buffer to be added after the last wash is calculated depending on the desired final absorbance of the dye at 540 nm.

Although DL-malic acid is the preferred reductant, other suitable reducing agents include citric acid, tartronic acids, DL-tartaric acid, mucic acid, including other alpha-hydroxy-dicarboxylic acids, lactic acid, tannic acid, ascorbic acid, and reducing sugars. Glutaraldehyde is the preferred coupling compound. Other useful coupling compounds include malonaldehyde bis(dimethyl acetal), water soluble aldehydes and dialdehydes. The pH of the reducing agent solution is important. Matching a given reductant to an optimal pH ensures the correct particle size for a given immunoassay reagent. Rigid control of the reaction time and temperature, mixing rate and configuration of the reaction vessel are also important.

Based on the above general procedure, the following reagents may be prepared:

i) Rubella assay—the antibody used is mouse antihuman IgG (20 mg/l of raw sol to be coated) dissolved in 2 ml of the phosphate buffer, as above. The final buffer is 10mM HEPES, 0.3M Mannitol, 0.5% BSA (monomeric), 0.2% sodium azide, pH 7.0. The final absorbance at 540 nm is 9–11.

ii) HCG assay—the appropriate antibody is anti-HCG clone $10A_5H_7$ (20 mg/l) dissolved in 1 ml of the phosphate buffer. The working buffer is 10 mM HEPES, 0.3M mannitol, 2.5% BSA (monomeric), 0 2% sodium azide, pH 7.0, and the final absorbance at 540 nm is 4.5–5.5.

iii) Ovulation test—the antibody used is anti-LH clone $29D_3C_4F_{12}$ (20 mg/l) in 0.1M sodium phosphate and 0.1% sodium azide, pH 7.4. The final buffer is 0.1M sodium phosphate, 0.15M sodium chloride, 5% D-mannitol, 1% monomeric BSA, 0.02% thimerosal, pH 7.4, and the final absorbance is 10.3.

iv) Toxic Shock Syndrome Toxin (TSST-1)—this dye preparation is the same as that described under rubella assay above.

A reagent having multiple specificities can also be prepared according to the method of this invention by mixing metal sol particles which have been previously coated with different specific immunochemical components, e.g., Human Immunodeficiency Virus Type 1 (HIV-1) specific probes for recombinant proteins (e.g., SP-120, SP-41, p31, p24). Likewise, HIV-2 markers, HAV, HBV, HCV, CMV, could be combined in various ways within a kit in accordance with a preselected format.

The invention is further illustrated by means of the following examples. These examples are meant to be illustrations only and are not intended to limit the present invention to the specific embodiments.

EXAMPLE 1

Preparation of Colloidal Gold Sol

All glassware surfaces which come in contact with colloidal gold sol should be siliconized utilizing 1% Silwet 720 (Union Carbide) by soaking 10 minutes and then rinsing with distilled water. 1 liter filtered distilled water is heated to 100° C. for at least 10 minutes. 10 ml of 1% gold chloride (Aldrich) in Milli-Q filtered distilled water is added to the reactor and mixed for one minute. 10 ml of 34 mM sodium citrate or 10 ml of 64 mM sodium malate or malic acid at pH 4.2 is added to the reactor to act as a reducing agent and rapid mixing continued for 20 minutes. A color change indicates successful formation of a gold sol. The heat source is then removed and the reactor cooled to 15°–30° C. 1 ml of 1% PEG 20,000 is added and the pH of the sol is adjusted to 7.1±0.1 pH with the addition of 0.1 molar $K_2CO_3$. The colloidal gold optical density is measured at 540 nm and at 600 nm. In this form, the gold sol is suitable for coupling to antibody. Colloidal gold thusly produced will be approximately 40–50 nm, as determined by the optical density ratio, such size being dependent on the chemical reducing conditions.

EXAMPLE 2

Colloidal Gold—Antibody Coupling

Procedure 1—Adsorptive Coupling

Antibody is dialyzed into 0.01M HEPES buffer solution at pH 7.1 using 12,000–14,000 molecular weight cut off dialysis tubing and 300 ml solution per ml of antibody for 18 hours and then filtered through a 0.45 μm SWINEX™ filter. The protein concentration of antibody is obtained by measuring the antibody's absorbance at 280 nm. The antibody is then diluted to a concentration of 3–4 mg/ml with 0.01 HEPES 7.1 to obtain optimal antibody—colloidal adsorption coupling as determined by the antibody to be labelled. With the sol present in the reactor from Example 1, the thusly filtered and diluted antibody is added while the sol is stirred at room temperature. Stirring is continued for approximately 30 minutes whereupon a buffer comprising 0.01M HEPES, 0.3M D-mannitol, 0.05% PEG 20,000, 0.1% BSA (RIA) grade and 0.05% sodium azide is added. Stirring is continued at room temperature for 30 minutes. The solution is then transferred to a high speed centrifuge, centrifuged and the supernatant removed. The sol is then washed four times utilizing the aforedescribed buffer and resuspended to 1/10 the starting sol concentration, filtered through a 0.45 μm membrane and stored at 2°–8° C.

Preferred Procedure 2—Covalent Coupling

An equivalent weight amount of BSA (100 mg BSA per 100 mg Sol) is added to the sol generated as described in Example 1 with pH preadjusted to 6.0. The mixture is stirred for 2 hours at room temperature and then filtered through a 0.22 micron membrane filter to remove large particles. The optical density is measured at 540 nm and 600 nm, and the optical density ratio calculated. The ratio of an acceptable material should be 2.50±0.30. 200 ml of the thusly prepared BSA-sol is then centrifuged at 25,000 G for 30 minutes and then wash once with distilled water. The washed particles are then mixed with 1% weight/volume glutaraldehyde and stirred for 2 hours. The mixture is then centrifuged at 25,000 G for 30 minutes and washed three times with distilled water. The activated and washed particles are then mixed with 2 mg of the appropriate purified monoclonal IgG in pH 7.4 phosphate buffer and stirred overnight at 2°–8° C. 2.5 mg sodium borohydride is added to stabilize the coupling. After stirring for 30 minutes, and quenching with 5 ml pH 8.0 glycine BSA buffer, the mixture is centrifuged at 25,000 G for 30 minutes and then washed three times with phosphate buffered saline pH 8.0. The coated gold is then resuspended and its concentration adjusted with a final pH 8.0 buffer comprising 50 mM triethanolamine, 100 mM NaCl, 0.2% BSA, 0.1% (NaN$_3$) to an optical density of approximately 10 at 540 nm. The coated sol is then filtered through a 0.22 micron filter and stored at 2°–8° C.

EXAMPLE 3

Sensitivity for LH in Urine

20 μls of colloidal gold labelled anti-LH antibody is added to two drops (100 μls) of urine sample and mixed in a test tube. One end of a membrane strip having anti-LH antibody applied thereto is dipped into a test tube. The following results using an LH standard prepared in concentration ranges from 0 mIU per ml to 200 mIU per ml was tested and the following results observed:

| | Sensitivity mIU/ml LH | | | | | |
|---|---|---|---|---|---|---|
| Standards | 0 | 5 | 15 | 40 | 100 | 200 |
| Observed Reaction | − | − | − | + | + | + |

EXAMPLE 4

Patient Samples

The procedure of Example 3 was followed utilizing urine samples from two women having 28 day menstrual cycles. The sample were collected over a five day period and the test results were verified by Advanced Care's Ovutime Test™ (Ortho Pharmaceutical Corporation) and the following results observed:

| Patient A | | | | | |
|---|---|---|---|---|---|
| Day in Cycle | 9 | 10 | 11 | 12 | 13 |
| Test Result | − | − | + | + | − |
| Ovutime Result | − | − | + | + | − |
| Patient B | | | | | |
| Day in Cycle | 9 | 10 | 11 | 12 | 13 |
| Test Result | − | − | + | + | − |
| Ovutime Result | − | − | + | + | − |

EXAMPLE 5

Ovulation Test with Built-in Test Control

A membrane strip was prepared pursuant to Example 3 except that the strip had two reagent bands. The lower band was coated with anti-LH antibody (forming the test band) and the upper band coated with LH (or hCG which reacts similarly due to cross-reactivity) serving as a control band. The colloidal gold labelled anti-LH antibody was prepared pursuant to Example 2. The procedure was as follows: 20 μls of colloidal gold labelled anti-LH antibody is added to a test tube along with 100 μls of urine sample and mixed. One end of the aforedescribed membrane strip is inserted into the mixture in the test tube and allowed to develop for five minutes. The results observed were as follows:

The same two women's urine sample A and B tested in Example 4 were tested confirming the same result. In addition, this test shows procedural test control band for all tests if it is done properly.

| Patient A | | | | | |
|---|---|---|---|---|---|
| Day in Cycle | 9 | 10 | 11 | 12 | 13 |
| Test band | − | − | + | + | − |
| Control band | + | + | + | + | + |
| Reference (Ovutime) | − | − | + | + | − |
| Patient B | | | | | |
| Day in Cycle | 9 | 10 | 11 | 12 | 13 |
| Test band | − | − | + | + | − |
| Control band | + | + | + | + | + |
| Reference (Ovutime) | − | − | + | + | − |

The foregoing procedure was repeated with the colloidal gold labelled antibody lyophilized in the test tube. Three drops (100 μls) of urine was added to the test tube and mixed and thereafter one end of the membrane strip was inserted and developed for five minutes. The observed results were identical.

The test was repeated with clinical samples:

|  | Number of Samples | Number Positive | Number Negative |
|---|---|---|---|
| Urine from Women | 24 | 6 | 18 |

Ovutime™ Reference Test was performed on the same samples and the results confirmed.

What we claim:

1. A method of producing a gold sol reagent containing gold sol particles of a preselected size, comprising:
   (a) reducing a gold containing solution at a selected pH to produce gold sol particles of a preselected size;
   (b) coating said gold particles directly with glutaraldehyde before covalently bonding said particles with at least one selected immunochemically reactive component; and
   (c) covalently bonding said coated particles with said immunochemically reactive component.

2. The method of claim 1 further comprising the step of optimizing the pH by selecting the pH and temperature and reductant so that particles of a preselected size are produced.

3. The method of claim 1 wherein the reducing step is performed at pH 4–5.5 and 70°–95° C. and the reducing agent is malic acid.

4. The method of claim 1 further comprising producing a Schiff's base between glutaraldehyde and the immunochemically reactive component and reducing the Schiff's base.

5. The method of claim 4 wherein the preselected size of the particles is between 30–60 nanometers.

* * * * *